United States Patent [19]
Polaschegg

[11] Patent Number: 5,725,773
[45] Date of Patent: Mar. 10, 1998

[54] METHOD AND APPARATUS FOR DETERMINING THE QUANTITY OF OREMIC TOXINS REMOVED BY A HEMODIALYSIS TREATMENT

[75] Inventor: Hans-Dietrich Polaschegg, Oberursel, Germany

[73] Assignee: Fresenius AG, Bad Homburg, Germany

[21] Appl. No.: 555,526

[22] Filed: Nov. 9, 1995

[30] Foreign Application Priority Data

Nov. 12, 1994 [DE] Germany ............... 44 40 556.1

[51] Int. Cl.⁶ ..................................... B01D 61/26
[52] U.S. Cl. .............. 210/636; 134/22.11; 134/166 R; 210/138; 210/321.69; 210/646; 210/739; 210/929; 422/68.1; 604/4
[58] Field of Search ............................ 210/87, 88, 89, 210/91, 92, 93, 96.2, 97, 138, 139, 141, 143, 321.65, 321.69, 321.71, 636, 646, 647, 739, 929, 194, 257.2; 604/4–6, 31; 204/415; 205/780.5, 793; 15/104.05; 134/22.1, 22.11, 166 R, 166 C; 137/563, 572; 285/130, 150; 422/68.1; 436/108, 180, 808

[56] References Cited

U.S. PATENT DOCUMENTS

| | | | |
|---|---|---|---|
| 3,869,354 | 3/1975 | Montalvo | 205/780.5 |
| 4,770,769 | 9/1988 | Schael | 210/96.2 |
| 5,308,315 | 5/1994 | Khuri et al. | 210/646 |
| 5,342,527 | 8/1994 | Chevallet et al. | 210/646 |
| 5,399,157 | 3/1995 | Goux et al. | 604/5 |
| 5,409,612 | 4/1995 | Maltais et al. | 210/636 |
| 5,486,286 | 1/1996 | Peterson et al. | 210/929 |
| 5,518,623 | 5/1996 | Keshaviah et al. | 210/646 |

FOREIGN PATENT DOCUMENTS

| | | |
|---|---|---|
| 2838414 | 10/1984 | Germany. |
| 3312909 | 9/1986 | Germany. |
| 3447989 | 7/1987 | Germany. |
| 4138140 | 5/1993 | Germany. |

OTHER PUBLICATIONS

A New Perspective on Cleaning and Disinfection, Clean-Cart©, brochure of Gambro Company, Sweden (undated).
B.J.Lankhorst et al., A Practical Guide to Kinetic Modeling Using the Technique of Direct Dialysis Quantification, Dialysis & Transplantation, vol. 12, Oct. 1983, pp. 694,696, 701–703,706.
A. Aviram et al., Dialysance of Amino Acids and Related Substances, Nephron 8, 1971 pp. 440–454.
A.W. Yu et al., Collection of Hemodialysate Aliquot Whose Composition Reflects That of Total Dialysate, Asaio Journal, p. 85, 1994 (Abstract).
H.D. Polaschegg, Methoden Und Geschichte Der Ultrafiltrationskontrolle in Der Hämodialyse, Das aktuelle Thema, Aktuelle Nephrologie, Jan. 1985, pp. 135–149.
John A. Sargent et al., Principles and Biophysics of Dialysis, Replacement of Renal Function by Dialysis, 3rd. Ed., pp. 87–143.

*Primary Examiner*—Joseph W. Drodge
*Attorney, Agent, or Firm*—W. G. Fasse; W. F. Wasse

[57] ABSTRACT

An apparatus and a method are provided for collecting samples of used dialysate during hemodialysis treatments. A fluid sample is branched off from the main flow of used dialysate into a sample receiving container. The branching off of the sample flow, i.e. withdrawal of the fluid sample, is either time- or volume-controlled so that during the course of a dialysis treatment a predetermined number of fluid samples are withdrawn, whereby the total sample volume has a prescribed ratio relative to the total volume of used dialysate. The recirculation and sample withdrawal conduit is selectively attachable to the sample receiving container for sample collection, or to the inlet of the hemodialysis device to form a recirculation loop for a disinfection cycle. A disinfectant cartridge can be interposed between the recirculation conduit and the hemodialysis device inlet.

23 Claims, 4 Drawing Sheets

FIG.1

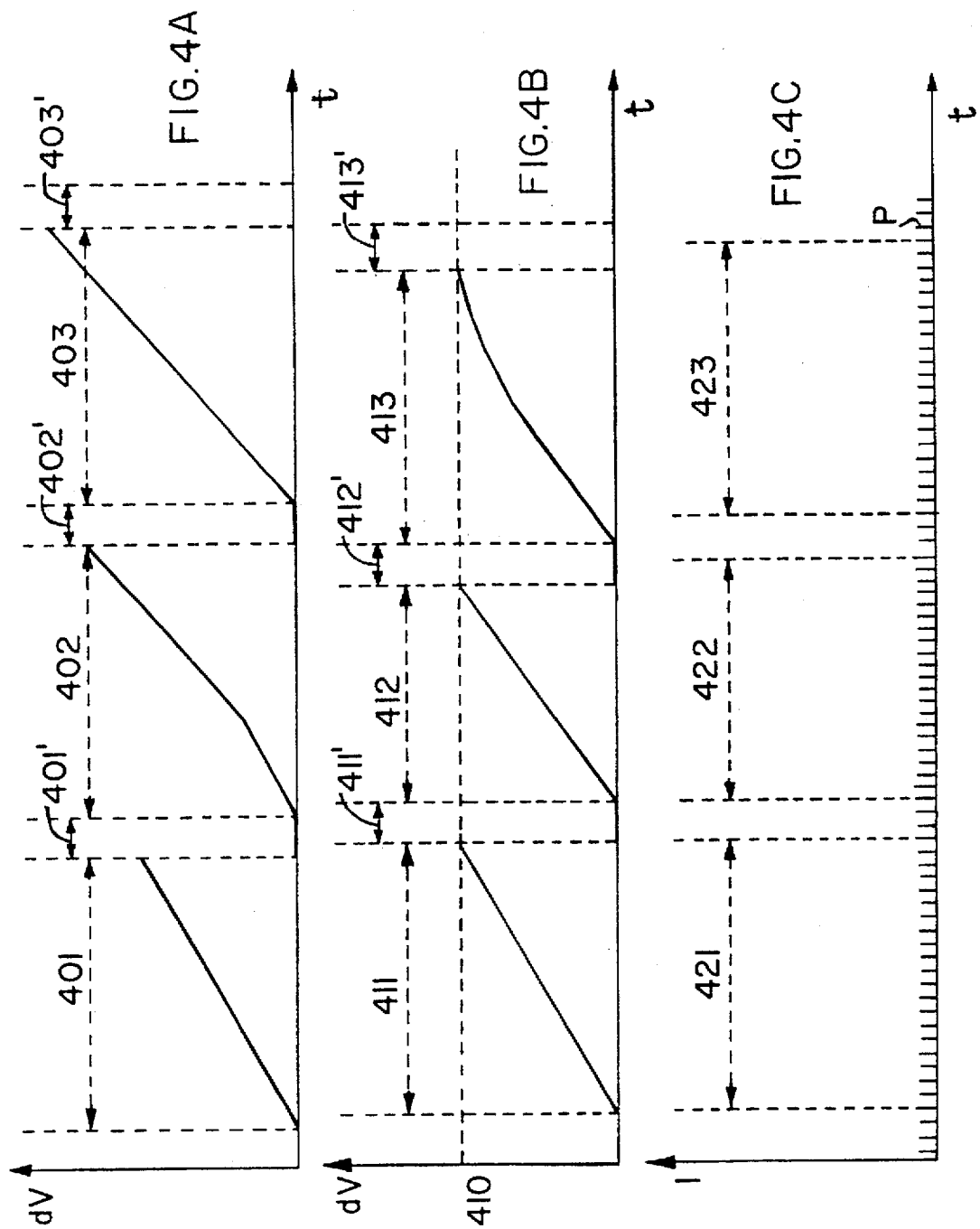

METHOD AND APPARATUS FOR DETERMINING THE QUANTITY OF OREMIC TOXINS REMOVED BY A HEMODIALYSIS TREATMENT

FIELD OF THE INVENTION

The invention relates to an apparatus and a method for determining the effectiveness of a hemodialysis treatment by determining the quantity of uremic toxins removed by the treatment.

BACKGROUND INFORMATION

Chronic hemodialysis treatment is the most widely used kidney replacement therapy. Approximately 500,000 patients live with such therapy because better alternatives, such as the transplantation of donated kidneys for example, is not available for them. The costs of treatment, which amount to a total of approximately U.S. $50,000 per year per patient, have placed an enormous burden on health insurance and the entire health care system. Only a portion of the total cost is directly related to the hemodialysis treatment itself, and the larger portion of the cost arises from various other treatments, patient stays in the hospital, blood supply and compatibility problems, transportation of patients to dialysis stations, and the like. However, the pressure to reduce medical costs is directed primarily at the actual dialysis treatment itself, since it is a standardized treatment and is carried out by large organizations.

The pressure to reduce treatment costs has lead to a reduction in the administered duration and often also the quantity of hemodialysis. In the United States of America, where approximately 92% of hemodialysis treatments are financed through the government organization Medicare, and where an extensive statistical medical data base exists, it has been observed that the survival probability of patients declined in the 1980s, which was attributed to a reduction in the dosage of dialysis per treatment. Based on this realization, research activities were intensified, with the goal of determining the minimum necessary and the optimal dialysis dosage. As a result thereof, more intensive research has also begun with the aim of discovering methods for determining the administered dialysis dosage in a reliable and cost effective manner. The emphasis on cost effectiveness and economy is important, because the underlying cause for these efforts has been one of cost reduction. A measuring method that substantially increases costs cannot serve the purpose of guaranteeing a sufficient dialysis treatment while holding the treatment costs constant, because in such a case the costs of the actual treatment must be further reduced to accommodate the costs of the measurement method.

A recognized method for determining the effectiveness of dialysis is based on urea kinetics. In this known method, the reduction of the plasma concentration of urea, from the beginning to the end of the hemodialysis treatment, is used as a measurement or yardstick for assessing the effectiveness of the dialysis. It is generally known that urea itself is not acutely toxic, and it is simply used in this case as a measurement reference substance. The urea kinetic method is, for example, completely described in the work of J. A. Sargent and F. A. Gotch, "Principles and Biophysics of Dialysis", published in "Replacement of Renal Function by Dialysis", 3rd. ed., J. F. Maher Editors, Kluwer Acadamic Publishers (1989), pages 87 to 143.

The standard urea kinetic method presumes a uniform distribution of urea in the whole body water volume, and is therefore called the one pool model. A complete measurement comprises at least three blood samples, namely one each respectively at the beginning and the end of the treatment and another one before beginning the next treatment. The urea concentration falls off exponentially during the dialysis. The exponential coefficient of this falling-off or decline of the urea concentration can be calculated from the above mentioned urea measurements at the beginning and at the end of the dialysis. The exponential coefficient is characterized by $K*T/V$, wherein K is the effective urea clearance, T is the dialysis time or duration, and V is the urea distribution volume, which is normally set equal to the whole body water volume. Through clinical observations it was determined that $K*T/V$ must be at least 1. From the second and third measurements of the above described measurement series, the quantity of the urea produced through metabolism can be determined, from which in turn, the quantity of the converted proteins, i.e. the protein catabolic rate, can be calculated, as described in the above mentioned work "Replacement of Renal Function by Dialysis". The protein catabolic rate is significant because it has been determined that the survival probability is very strongly dependent on the plasma albumin content which in turn is dependent on the protein uptake.

For treatments with a reduced dialysis time and a simultaneously increased urea clearance, the actual process is inadequately described by the above described one pool model. In this context, the error can entail up to 40%. The art has therefore transitioned to so-called two pool models, the characterization of which requires at least three intradialytic blood samples, whereby the last sample is taken approximately 30 to 60 minutes after ending the hemodialysis treatment. This has further complicated the characterization of the treatment quantity.

Since the beginning of hemodialysis treatment technology, it has been attempted to measure the removed uremic toxins in the exchange fluid. In order to achieve that, all of the used dialysis fluid was collected and the quantity was measured, as described for example by B. J. Lankhorst, P. Ellis, C. Nosse, P. Malchesky, and M. O. Magnusson in "A Practical Guide to Kinetic Modeling Using the Technique of Direct Dialysis Quantification", published in "Dialysis & Transplantation" (1983), Number 12, pages 694 to 706. The concentration of urea and other uremic toxins in a sample of this dialysis fluid was measured and then multiplied by the total quantity of the dialysis fluid to determine the total quantity of the removed substance. This method is, however, too impractical for routine use, because it involves collecting, weighing and mixing more than 100 liters of dialysis fluid. Finally, it has also been discovered, that urea is quickly metabolized by bacteria, that used dialysis fluid is usually strongly contaminated by bacteria, and that therefore the measured urea concentration is not the true urea concentration.

In order to avoid the problem of the great quantities of fluid that must be collected and measured, it has been suggested to only collect a portion of the used dialysis fluid. This method is called partial dialysate collection. In this method, approximately 1% of the used dialysis fluid is collected in a continuous manner. At the end, the collected quantity is weighed, mixed, and then a sample is withdrawn and analyzed. The concentration determined in the sample is multiplied by the quantity and then multiplied by the proportional factor defined by the ratio of the total dialysate relative to the collected dialysate, which gives the total removed quantity. This method effectively avoids the quantity problem, but does not avoid the bacterial contamination problem. As a further step, the partial quantity of used dialysis fluid specified for collection can be passed through a sterile filter into the sample collecting container. This solves the problem of bacterial contamination, but entails increased costs.

Several methods are known for carrying out a partial dialysate collection. For example, German Patent 3,312,909, Oct. 18, 1984, (Inventors S. Stiller and U. Schafer, Assignee S. Stiller) entitled "Passiver Flüssigkeits-stromteiler" ("Passive Fluid Flow Splitter") describes a passive flow divider or flow splitter in which the total dialysate flow is directed through a plurality of capillaries. A partial flow is extracted from one or more capillaries for achieving the partial dialysate collection. A disadvantage of this known arrangement is that even slight variations in the flow can alter the flow splitter ratio, without being noticeable. The same disadvantage applies to an arrangement in which a cannula is introduced into the dialysate flow, for example as described by T. S. Ing, A. W. Yu, M. N. Khalaf, P. Tiwari, M. Rafiq, A. A. Khan, and Z. M. Nawab in "Collection of Hemodialysate Aliquot Whose Composition Reflects That of Total Dialysate", ASAIO Abstracts (1994), page 85.

Another known apparatus uses a pump that extracts a partial stream out of the dialysate stream, as described by A. Aviram, J. H. Peters, and P. F. Gulyassy, in "Dialysance of Amino Acids and Related Substances", published in Nephron (1971), Number 8, pages 440 to 454. A disadvantage of this system is that the dialysate flow must be held constant, or else the rate of the partial streampump must be correspondingly adjusted in a following manner.

The methods of operating the two above described apparatus have the disadvantage that the sample is to be extracted from an area of the hydraulic system that is usually bacterially contaminated, and that is never disinfected or sterilized in the typical devices in which sterilization or disinfection is achieved by a recirculation cycle. In other words, the sample is extracted from a part of the hydraulic circuit that is not within the recirculation loop.

Hemodialysis devices must be disinfected from time to time, typically at least once daily. These devices are continuously recontaminated, for example by non-sterile water, non-sterile dialysis fluid concentrate, and also through the procedure of connecting dialysers, which is normally not carried out in an aseptic manner at least on the dialysis fluid side of the dialyser. In some devices, disinfection is carried out by heating the in-flowing water to greater than 85° C., or by mixing-in a disinfecting medium. Between those two methods, the heating method is becoming ever more preferred, because it is carried out without potentially environmentally dangerous disinfectant materials. However, it has the disadvantage that germs present in the water might not be completely killed due to the short circulation time. Thus, if the water supply is contaminated, the device will be continuously recontaminated.

Some dialysis devices use dialysate filters arranged to sterilely filter the dialysate directly before the dialyser. These filters must themselves be flushed out, which is normally carried out during the disinfection process. Thereby, germs present at the dialyser connection manage to flow past and to the outlet conduit, which is thereby recontaminated.

Therefore, devices have been developed which prevent a continual recontamination by switching the device, after an initial flushing and cleaning phase, in such a manner that water or disinfecting solution is recirculated through the device. In that manner, the device is disconnected from both the inlet and the outlet so that it cannot be recontaminated. Such an apparatus is described, for example, in German Patent 3,447,989, of Jul. 16, 1987, (inventor H. D. Polaschegg, Assignee Fresenius AG) entitled "H ämodialysevorrichtung" ("Hemodialysis Apparatus"). The addition of disinfecting medium can be achieved by interposing a disinfecting medium container in the recirculation circuit, as described, for example, in German Patent 4,138, 140, of Dec. 23, 1993, (inventor H. D. Polaschegg, Assignee Fresenius AG) entitled "Vorrichtung zur Desinfektion von H ämodialysegeräten mit einem pulverförmigen Konzentrat" ("Apparatus for Disinfecting Hemodialysis Apparatus Using a Powdered Concentrate"). A disadvantage of the above described methods and apparatus is that the partial stream for sampling is typically withdrawn from the drain conduit, which is not disinfected.

OBJECTS OF THE INVENTION

In view of the above it is the aim of the invention to achieve the following objects singly or in combination:

to provide a method and apparatus that avoids the above described disadvantages;

to provide such a method and apparatus that can economically achieve a cost optimization of the required dialysis dosage;

to provide a method and apparatus that makes it possible to determine the quantity of removed uremic toxins in a dialysis device with minimum additional hardware and without requiring blood sampling;

to avoid the problems associated with the collection and measurement of large quantities of dialysis fluid to measure urea concentration in carrying out a hemodialysis treatment;

to avoid the problems of bacterial contamination in the outlet conduit of a hemodialysis device, and to provide a simplified process for disinfecting a hemodialysis device in such a manner that the results of determining the quantity of uremic toxins are not impaired through bacterial contamination; and to provide a particular control sequence for carrying out the withdrawal of samples of dialysis fluid from a hemodialysis device.

SUMMARY OF THE INVENTION

The above objects have been achieved in a method and apparatus according to the present invention. The apparatus of the present invention allows a partial dialysate collection to be carried out in a contamination-free manner, in a hemodialysis device that is disinfected or sterilized with a recirculation procedure. To achieve this, the recirculation branch of the hemodialysis device circuit is alternatively closed to form the recirculation loop or opened for withdrawing a sample, for which a partial stream of the used dialysis fluid is withdrawn using a valve arrangement.

The apparatus preferably includes two valves to switch between disinfecting/recirculating operation and dialysis operation. During dialysis operation, the valves switch between two operating conditions, namely sample withdrawing and draining, as directed by a control unit in a time-controlled or volume-controlled manner. To provide a simplified disinfecting process, the inventive apparatus can include a container or cartridge containing a disinfecting medium concentrate, which is interposed in the recirculation circuit.

BRIEF DESCRIPTION OF THE DRAWINGS

In order that the invention may be clearly understood, it will now be described, by way of example, with reference to the accompanying drawings, wherein:

FIGS. 4A to 4C are time diagrams for three alternative embodiments of controlling the operation of the apparatus according to the present invention.

DETAILED DESCRIPTION OF PREFERRED EXAMPLE EMBODIMENTS AND OF THE BEST MODE OF THE INVENTION

Figure 1:
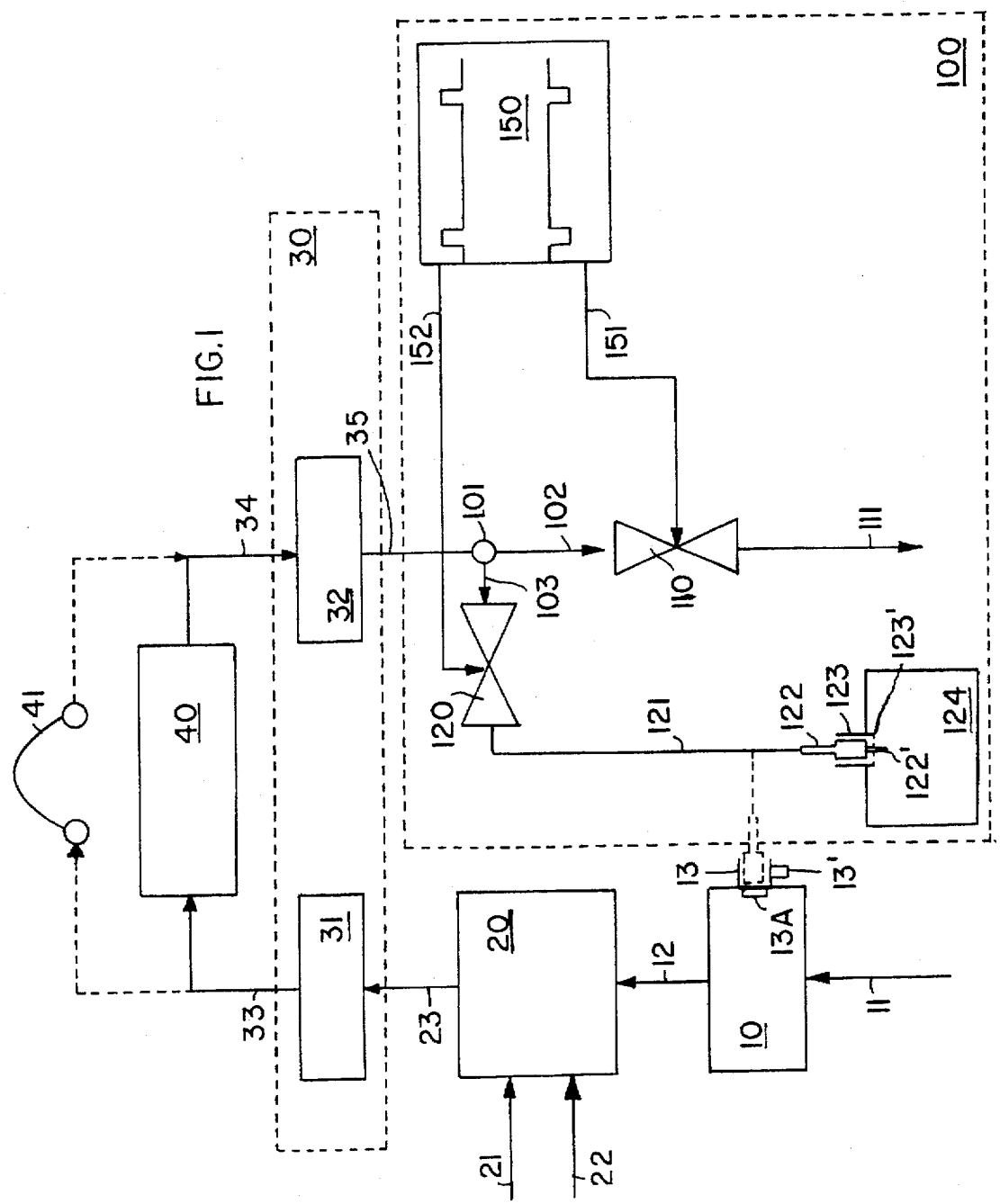
FIG. 1 is a schematic block circuit diagram showing a dialysis device including an embodiment of the apparatus according to the present invention.

FIG. 1 is a block circuit diagram representing the flow circuit of a dialysis device that includes the apparatus according to the invention. The dialysis device includes components relating to the water inlet, dialysate preparation, fluid balancing, sample withdrawal, and disinfection and sterilization as described in the following.

Relating to the water inlet, water suitable for hemodialysis is supplied from a water source that is not shown in detail, through a conduit 11 and into an inlet container 10. From there, a connection conduit 12 leads to the dialysate preparation unit 20. A plug-in connector member such as a socket 13 is provided on the water inlet container 10, to allow the inlet container 10 to be connected to a recirculation circuit consisting of elements 103, 120, 121 and 122 as described below.

Relating to the preparation of dialysate, hemodialysis concentrates are provided through conduits 21 and 22 into the dialysate preparation unit 20. Typically, the hemodialysis concentrates are so-called acid concentrate and bicarbonate concentrate, but instead of these two concentrates a single concentrate may be provided, or as a further alternative, more than two concentrates may be provided. In the latter case more supply conduits are necessary. In the dialysate preparation unit 20, the dialysate is mixed, warmed to a proper temperature, and degassed. Through a conduit 23, the prepared dialysate flows into the fluid balancing unit 30.

For carrying out the balancing of fluid, the apparatus comprises a fluid balancing unit 30 that can be a system based on balance chambers or a system based on flow measuring devices. Such systems are, for example, described in the work of the present inventor, namely "Methoden und Geschichte der Ultrafiltrationskontrolle in der Hämodialyse" ("Methods and History of Ultrafiltration Control in Hemodialysis") by H. D. Polaschegg, Wiss. Info. Fresenius Stiftung Aktuelle Nephrologie (1985), number 18, pages 135 to 149.

As shown in FIG. 1, the balancing unit 30 may comprise a flow measuring or control apparatus 31 for the fresh dialysate. From there the fresh dialysate passes through a conduit 33 and a plug-in connection (not shown in detail) to a dialyzer 40. Alternatively, the conduit 33 can be connected to a short-circuit member 41 instead of the dialyzer 40, in order to carry out the cleaning and disinfection of the hemodialysis device after completion of a dialysis treatment. From the dialyzer 40 or the short-circuit member 41, the fluid (which will be used dialysis fluid in the event that dialysis has been carried out in the dialyser 40) flows to the outlet-side flow measuring or control apparatus 32 and from there through a conduit 35 to the inventive sampling and recirculation unit 100. Various components such as monitoring and protective devices for monitoring the proper composition of the dialysis fluid and the proper functioning of the fluid balancing apparatus are not shown, but are well understood as such by persons of ordinary skill in the art.

The invention is particularly directed to a special method and apparatus for withdrawing fluid samples. In this regard, the sampling and recirculation unit 100 comprises a branching element 101, to which used dialysis fluid is provided through the conduit 35. From the branching element 101, fluid either: flows through conduit 102, fluid outlet shut-off valve 110 and drain conduit 111 to a used fluid drain during a draining period; or alternatively flows through conduit 103, sample withdrawal shut-off valve 120, and conduit 121 to a plug-in connector plug 122 provided at a free end of the conduit 121, during a sampling period of the dialysis cycle or during a recirculation/disinfection cycle. As an alternative embodiment, the two shut-off valves 110 and 120 can be incorporated in a single valve arrangement, for example a path selector valve having one inlet port and two outlet ports, wherein the flow can be alternatively selectively directed to either one or the other outlet port or completely shut off.

As shown by solid lines in FIG. 1, the plug-in connector plug 122 can be plugged into a connector socket 123 provided on a sample collection container 124, for collecting dialysate samples in the container 124 during the sampling periods of the hemodialysis cycle. Alternatively, as shown by dashed lines in FIG. 1, the connector plug 122 can be plugged into, i.e. connected with, the socket 13 provided on the water inlet container 10, whereby a recirculation circuit is established for carrying out a disinfection or sterilization cycle.

Regarding the collection of dialysate samples, the container 124 should typically have a volume capacity of two liters, which corresponds to approximately 2% of the dialysis fluid that is used in the course of a dialysis treatment. The container 124 may be a rigid container, but is preferably a flexible bag made of a material having a low gas permeability, which prevents $CO_2$ from escaping out of the dialysate, which would lead to an alteration of the pH value. A sterile or sterilizable bag is preferred. The container 124 is most preferably made of a low gas permeability material and has an opening that is sterilely sealed by a septum or membrane, for example made of rubber, that can be pierced by a fluid tapping needle for filling fluid into the container. It is especially cost economical to use a septum or membrane 123' as the plug-in connector socket 123 provided on the container 124. With such an embodiment, the plug-in connector plug 122 provided on the conduit 121 then preferably comprises a piercing or fluid tapping needle connector 122', as is commonly known from infusion lines, which projects out of a lockable plug-in connector. The coupling or socket 13 on the water inlet container then preferably comprises a mating countermember for this lockable plug-in connector. The lockable plug-in connector may, for example, be a Luer-Lock connector, as it is commonly known in the field of medical technology.

Figure 3:
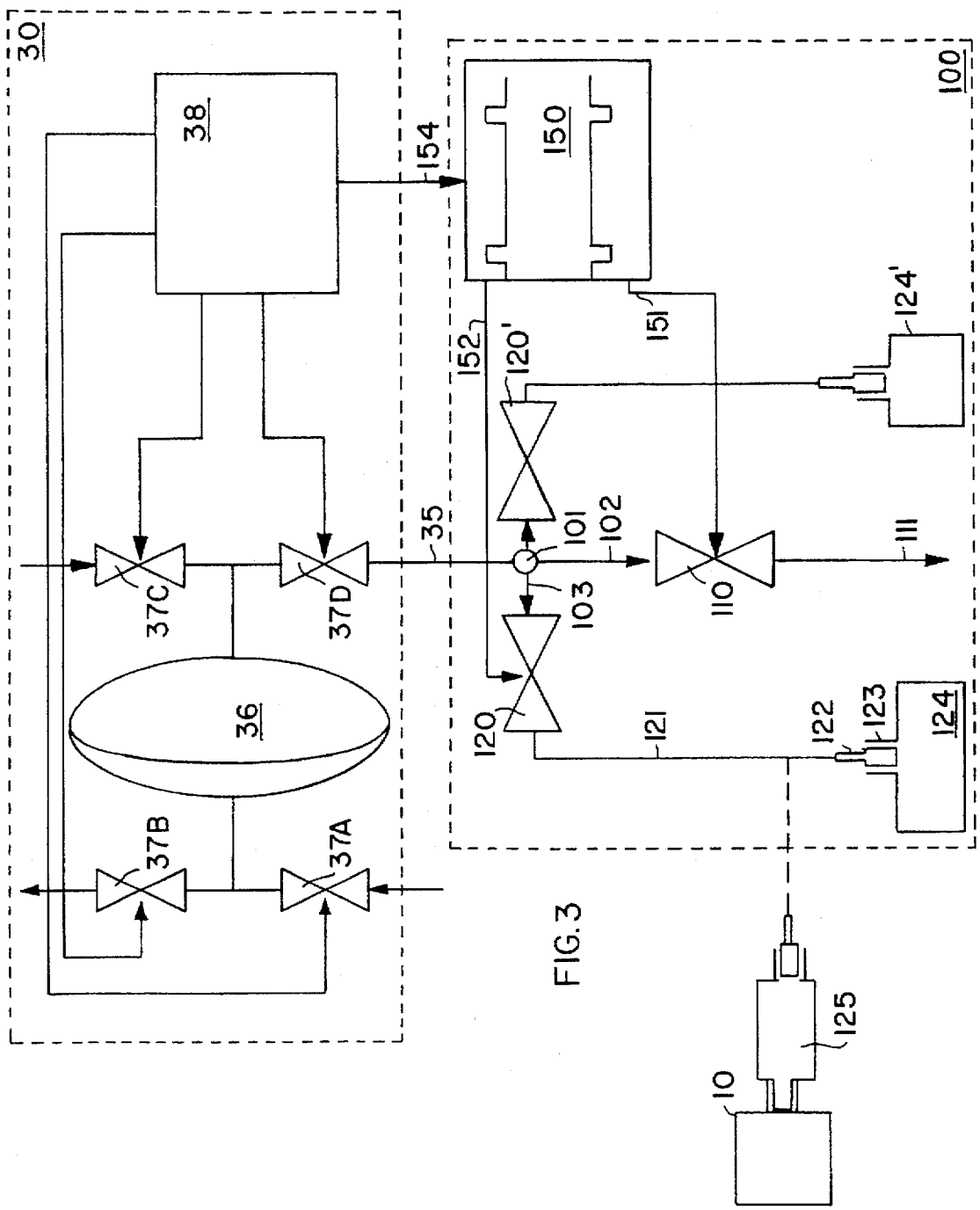
FIG. 3 is a schematic block circuit diagram showing a portion of the diagram of FIG. 1, and showing another embodiment of a switching control operating in conjunction with a balancing device, according to the invention.

For carrying out the disinfection cycle, it is further possible to interpose a container or cartridge 125 of a liquid or solid disinfecting medium concentrate between the connector plug 122 and the socket 13, for example as shown by dashed lines in FIG. 3. Such an arrangement is generally described in the prospectus CleanCart™ of the company Gambro, Lund, Sweden. In this arrangement, the disinfecting solution is formed as the fluid, e.g. water, is recirculated through the recirculation loop including the cartridge 125. The cartridge 125 includes appropriate connectors for mating with the connector plug 122 and the socket 13.

The shut-off valves 110 and 120 are controlled by a control arrangement 150. If it is not desired to withdraw a fluid sample, then valve 120 remains closed and valve 110 remains open in a dialysis operation. For carrying out a controlled sampling, i.e. withdrawal of fluid samples, valve 110 is closed while valve 120 is opened, preferably at regular or uniform time intervals. In other words, in normal dialysis operation, valve 110 is open so that the used dialysis fluid simply flows out conduit 111 to the outlet drain, while valve 120 is closed. When a sample is to be withdrawn, the valve 110 is closed and the valve 120 is opened so that used fluid flows through conduit 121 into the sample collection container 124. During a disinfecting recirculation cycle, valve 110 is closed, valve 120 is open, and the plug-in connector plug 122 is plugged into the socket 13. Specific flow conditions and examples will be described below.

The respective open time of the two valves is selected and controlled in such a manner that the ratio of the valve open times corresponds to the desired ratio of the sample amount relative to the total amount of dialysis fluid that is used. The preferred sample amount is 1 to 2%. The frequency of sample withdrawal should be at least three times per dialysis treatment, and the upper limit thereof is limited only by the switching speed of the valves. Preferably, the switching or sampling frequency is between 30 and 100 times per dialysis treatment. Thus, for a dialysis duration of 3 hours (180 minutes), a switching frequency of 30 samples per dialysis treatment results in respective switching intervals of 6 minutes each, whereby the sample withdrawal valve 120 is respectively open for 7.2 seconds in each interval to amount to 2% of the total time.

To carry out a disinfection or sterilization cycle, as already described, the connector plug 122 is connected with the plug-in socket 13. For a period of typically 5 minutes after beginning the disinfection cycle, the valve 110 remains open and the valve 120 remains closed in order to flush any remaining dialysis fluid out of the dialysis device, through the conduit 111 and out to a drain. Thereafter, valve 110 is closed and valve 120 is opened, while simultaneously the water and the concentrate supply to the dialysis device is interrupted or shut-off in a manner that is not shown in detail, but that will be readily understood to persons of ordinary skill in the art. The water present in the dialysis device has either been heated and/or replaced by a disinfecting medium, which then recirculates in a generally known manner through the hemodialysis device so as to disinfect or sterilize the device.

The further detailed embodiment of the invention relates to controlling the outlet valve 110 and the sample valve 120. In the following discussion, the sample withdrawal interval is designated to be the period of time from opening the outlet valve 110 until the next subsequent opening of the outlet valve 110. Thus, the sample withdrawal interval begins upon opening the outlet valve, continues during and includes closing the outlet valve and finally ends upon reopening the outlet valve. The sample withdrawal valve 120 is closed at the beginning of the sample withdrawal interval, is then opened during the interval, and is again closed at the end of the sample withdrawal interval.

The control of the sample withdrawal valve and the outlet valve can be carried out in a purely time-dependent manner, as already described. Alternatively, in order to compensate for variations in the dialysate flow rate or in the pressure conditions, especially during long sampling time intervals, the control can also be carried out in a volume-dependent manner. To achieve this, a flow measuring unit is interposed into the dialysate conduit upstream of the branching point 101 (as described in more detail in an example embodiment below). Then, for each time interval, the open period of the sample withdrawal valve 120 is controlled in such a manner that the sample quantity is in the prescribed proportion relative to the total quantity measured during the sample withdrawal interval. If the flow increases during a sample withdrawal interval, which means that the processed dialysate volume increases, then the sample withdrawal valve 120 is opened for a shorter time period, in order to hold the volume ratio constant.

As a further alternative, and in a similar manner, the opening time of the sample withdrawal valve 120 can be controlled by using a volume sensor. In this case, the valves 110 and 120 are controlled in such a manner that the volume ratio corresponds to the prescribed ratio, whereby the time interval is prescribed. The control thus ensures that although the sample withdrawal takes place in a fixed time interval, the sample withdrawal volume is matched or correlated to the dialysate volume processed, i.e. passing through, during the opening time interval of the outlet valve 110. If the hemodialysis device uses a volumetric fluid balancing unit, then the volume measuring device 32 for used dialysate can simultaneously serve as a measuring device for controlling the valves 110 and 120. As another alternative, the control of the valves 110 and 120 can be carried out in such a manner that the sample withdrawal valve is respectively opened at the time when a predetermined dialysate quantity has been reached.

If the hemodialysis device uses a volumetric UF control with balance chambers, for example as described in U.S. Pat. No. 4,770,769 (Schael), issued Sep. 13, 1988, and entitled "Hemodialysis Apparatus With Degassing Means for the Dialysis Solution" and corresponding German Patent 2,838,414 (inventor W. Schael W, assignee Fresenius AG) entitled "Vorrichtung zur Hämodialyse und zum Entziehen von Ultrafiltrat", then the balance chamber circuit control can also be used for controlling the sample withdrawal. To achieve this, the sample withdrawal valve is switched synchronously with each $n^{th}$ balance chamber switchover, whereby n is the flow divider ratio, Which, for example, is typically 30 to 100 for a balance chamber fill volume of 30 ml.

Figure 2:
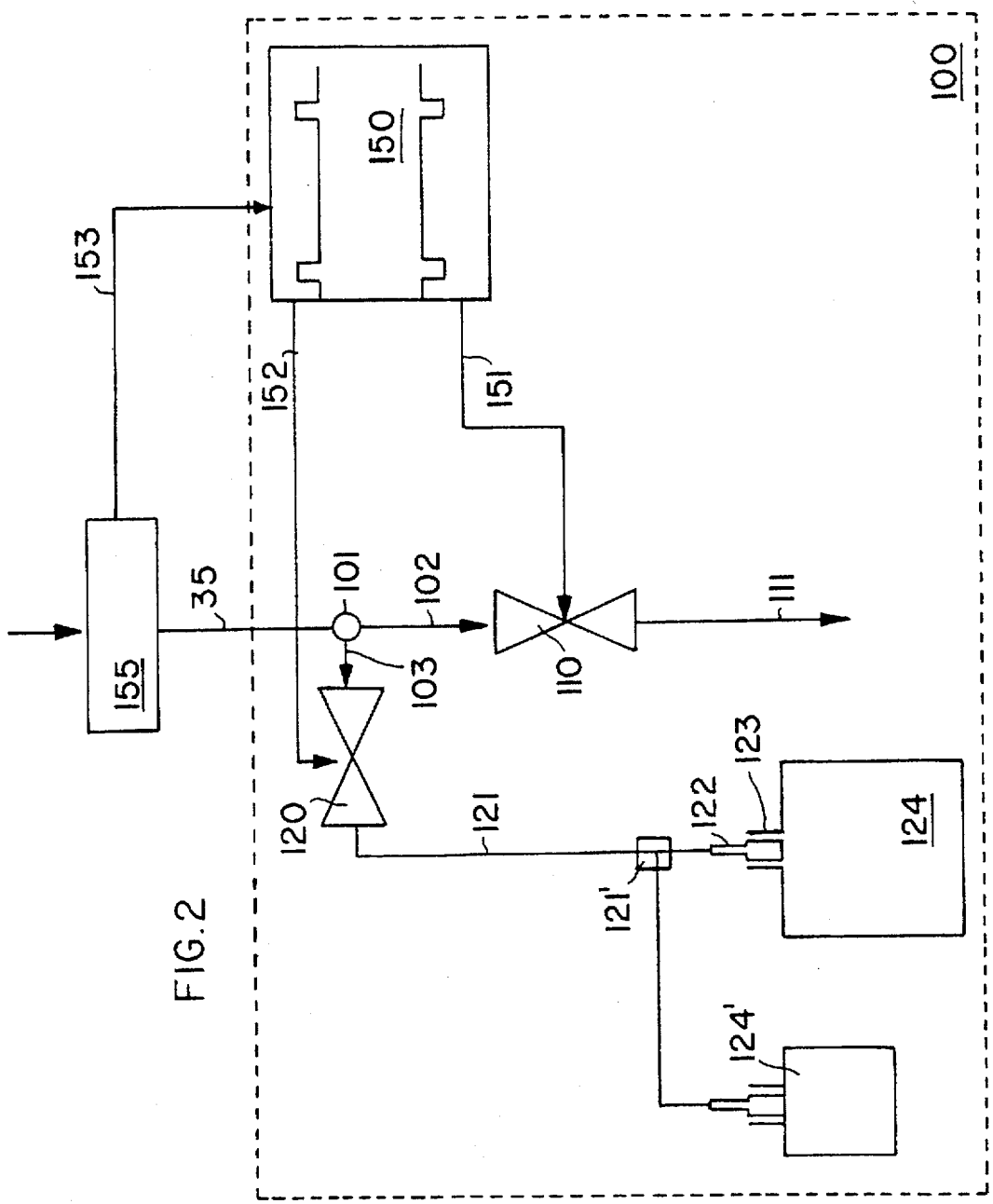
FIG. 2 is a schematic block circuit diagram showing a portion of the diagram of FIG. 1, and showing a particular embodiment of a switching control arrangement according to the invention.

The embodiments of the invention that have been generally described above are shown with more detail in FIGS. 2, 3, and 4A to 4C. FIG. 2 shows a portion of the circuit of FIG. 1, and additionally shows a flow measuring apparatus 155 for measuring the flow of the used dialysate, and a line 153 connecting the measuring apparatus 155 to the control apparatus 150. If the hemodialysis device uses a fluid balancing apparatus including flow measuring devices, then this apparatus shown in FIG. 2 can also be employed. In such a case, the flow measuring apparatus 155 is identical to the measuring apparatus 32 for used dialysate discussed above.

FIG. 3 also shows a portion of FIG. 1, with a different embodiment of a fluid balancing apparatus 30 that uses a balance chamber 36. Instead of a single balance chamber 36, it is possible to use two or more balance chambers. The fluid balancing apparatus 30 further comprises four valves 37A, 37B, 37C and 37D and a control unit 38 that controls the valves 37 in such a manner that the valves 37A and 37D are respectively open while the valves 37B and 37C are closed during a filling phase. From this state, the balance chamber is switched over into the circulation phase, whereby the valves 37B and 37C are opened and the valves 37A and 37D are closed. Furthermore, a signal line 154 connects the balance chamber control unit 38 to the sample withdrawal control unit 150. Thus, as described above, the control unit 38 can provide control signals for carrying out the sampling according to the present invention.

FIGS. 4A to 4C are respective time progression diagrams schematically showing the manner of operating the sample withdrawal control unit 150 for the embodiments of the invention described above with reference to FIGS. 2 and 3. FIG. 4A shows the control of the sample withdrawal valve 120 using the arrangement shown in FIG. 2, wherein a flow measuring device is used for measuring the used dialysate. In the diagram, the horizontal axis is a time axis and is labelled "t". The vertical axis is an incremental volume axis and is labelled "dV" indicating the volume flowing through the outlet valve 110 in a time interval. In this context, the outlet valve 110 respectively remains open for a prescribed time interval. Thus, open time intervals 401, 402, and 403 of the outlet valve 110 (i.e. drain periods) representing three different example situations all have the same duration, bounded by dashed lines in the drawing. In shorter time intervals 401', 402' and 403' or sampling periods respectively following the drain period intervals 401, 402 and 403, the outlet valve 110 is closed and the sample withdrawal valve 120 is open. If the flow varies during the open time interval of the outlet valve 110 (i.e. interval 401, 402, or 403), then the closed time of valve 110, i.e. the open time of the valve 120 (i.e. interval 401', 402' or 403') will be correspondingly adjusted, as discussed in detail next.

In FIG. 4A, the flow is constant during time interval 401, which leads to a linear increase in the processed volume dV of fluid. In time interval 402 the volume does not increase linearly, because the flow increases toward the end of the time interval. Since the flow at the end of the interval 402 (and thus for the beginning of interval 402') is greater than the average flow during the interval 402, the subsequent open time interval 402' of the sample withdrawal valve 120 is controlled in such a manner that the volume ratio of the sample quantity relative to the total quantity of used dialysate corresponds to the prescribed ratio. In the present case, this leads to a time reduction of the open time interval 402'.

The open time interval can be calculated according to the following equation:

$$tp = \frac{V}{q(T)} * \frac{F}{1-F} \qquad \text{Equation (1)}$$

wherein V is the volume flowing through during the open time interval of the outlet valve 110, q(T) is the time dependent flow of used dialysate at the end of the interval T, whereby the starting time of the interval is respectively set to zero, tp is the open time of the sample withdrawal valve 120, and F is the prescribed ratio of the sample quantity relative to the total quantity of dialysis fluid, for example 0.03.

Alternatively, the open time of the sample withdrawal valve 120 can be controlled by the flow measuring device. In this case, the sample withdrawal valve is kept open until the sample volume Vp is equal to the prescribed proportion F relative to the total quantity. Then the fluid quantity delivered during the open time interval of the outlet valve 110 corresponds to 1-F.

In the last example in FIG. 4A, i.e. in time interval 403, the flow is constant at a higher rate than in time interval 401, which results in a linear increase in the process volume dV that reaches a higher sum processed volume at the end of the time interval 403. The subsequent open time interval 403' of the sample withdrawal valve 120 is appropriately set to take this into account.

FIG. 4B shows another alternative for controlling the open time of the sample withdrawal valve, i.e. the sampling period. The outlet valve 110 is respectively closed and the sample withdrawal valve 120 is respectively opened whenever a predetermined quantity of used dialysis fluid, for example 1 liter, is reached, i.e. has flowed through the outlet valve. This predetermined quantity is shown in FIG. 4B with a dashed line 410. FIG. 4B schematically shows a first time interval 411 having a constant flow and a certain corresponding interval duration to reach the predetermined quantity 410. The next time interval 412 also has a constant flow, but with a greater flow magnitude than that during interval 411. Thus, the time duration of interval 412 is shorter than the time duration of interval 411. The last time interval 413 has a decreasing flow. As a result, the time intervals 411, 412, and 413 have different time durations. The open time of the sample withdrawal valve, i.e. the durations of the intervals 411', 412' and 413', can either be calculated according to the above Equation (1), or can be controlled using the flow measuring device as already described.

FIG. 4C shows another alternative for controlling the open time of the valves in the event that a volume measuring device with balance chambers is being used. In the time diagram of FIG. 4C, the balance chamber switching pulses are indicated as short lines or tick marks P above the time axis. The outlet valve is opened for a prescribed number of balance chamber switching impulses (e.g. 20 impulses in the illustrated example), and then the outlet valve 110 is closed and the sample withdrawal valve 120 is opened for another prescribed number of impulses (e.g. 3 impulses in the illustrated example). Since one balance chamber stroke respectively corresponds to a precise predetermined volume of fluid, a precisely defined ratio between the sample volume and the total volume results, which is independent of the flow and which corresponds to the ratio F. In the illustrated example, F=3/23. The time durations of the sample withdrawal intervals are thereby dependent on the flow rate. For example, in FIG. 4C it is assumed that the flow is increased during interval 422, whereby the time spacings between the balance chamber impulses P are smaller and the total duration of the interval 422 is correspondingly shorter than that of the adjacent intervals.

The method of partial dialysate collection allows the quantity of removed substance to be calculated, but it provides no information regarding the kinetics of this process, that is to say, for example, whether the reduction or decline of the concentration over time corresponds to a one pool or a two pool model. Thus, a further embodiment of the invention provides additional sample withdrawal valves arranged in the circuit in parallel with the above described valve 120, for example an additional sample withdrawal valve 120' shown in FIG. 3. With such an additional valve 120', it is possible to withdraw single samples at the beginning and at the end of the dialysis treatment into an additional sample container 124'. From these additional samples, or in combination with the dialysate sample collected over the entire dialysis duration in container 124, various items of information regarding the kinetics of the process can be determined. Instead of providing several sample withdrawal valves, a switchable sample withdrawal selector 121' (see e.g. FIG. 2) can be arranged in the conduit 121 downstream of the valve 120. The sample withdrawal selector 121' is essentially a switching apparatus for directing a sample fluid quantity to a selected one of several sample containers, e.g. 124 or 124'. The switching apparatus 121' itself comprises several valves leading to the several containers or comprises a container exchanging apparatus.

As further details of the apparatus of the invention, the coupling member 13 may include a safety valve 13A such as a non-return valve or an automatic closing mechanism that closes the hole of the coupling member 13 when the plug 122 is not connected thereto. Furthermore, a sensor 13' can be arranged on the coupling member 13 to detect when the plug 122 is connected to the coupling member 13, and the sensor 13' can be connected for signal transmission to the circuit controller. If the sensor 13' detects that the plug 122 is connected to the coupling member 13 during a hemodialysis treatment, then the sample withdrawal valve 120 is closed and the outlet valve 110 is opened, regardless and independent of a sample withdrawal program that may be running. Thus, the sample withdrawal program is interrupted, or starting of the sample withdrawal program is prevented. In this manner, the recirculation of used dialysate during a hemodialysis treatment is prevented.

During a disinfection cycle operating in the recirculation mode, the sample withdrawal valve 120 remains open and the outlet valve 110 remains closed. The disinfection program can only be started if the sensor 13' detects that the plug 122 is connected to the coupling member 13. In the case that the sensor 13' detects a release or disconnection of the plug 122 from the coupling member 13 during a disinfection cycle, the disinfection program is interrupted and the sample withdrawal valve 120 is closed. The sensor 13' may, for example, be a mechanical microswitch, a magnetic sensor, or an optical sensor.

Although the invention has been described with reference to specific example embodiments, it will be appreciated that it is intended to cover all modifications and equivalents within the scope of the appended claims.

What is claimed is:

1. A hemodialysis device for carrying out a dialysis treatment using a dialyzer, collecting a portion of used dialysis fluid as a fluid sample during said treatment, and carrying out a recirculating disinfection cycle separately from said dialysis treatment by circulating a disinfecting medium through a disinfection recirculation conduit branch, said device including a fresh fluid conduit with a fluid inlet arrangement at its upstream end, a used fluid conduit with a fluid outlet at its downstream end, and a fluid sampling and recirculating apparatus connected to said fluid outlet, wherein said fresh fluid conduit and said used fluid conduit are arranged and adapted to have a dialyzer connected therebetween during said dialysis treatment with said fresh fluid conduit upstream from the dialyzer and said used fluid conduit downstream from the dialyzer, wherein said fluid sampling and recirculating apparatus comprises a drain conduit, a sampling and recirculating conduit with a first plug-in connector member at a downstream end thereof, a switching valve arrangement connected to said fluid outlet and selectively connecting said fluid outlet for fluid flow to said drain conduit or to said sampling and recirculating conduit in exclusive alternating succession, a control unit connected for control signal transmission to said valve arrangement, and a fluid sample receiving container with a second plug-in connector member adapted to be connectable with said first plug-in connector member to collect in said container said portion of said used dialysis fluid as said fluid sample during said dialysis treatment, and wherein said fluid inlet arrangement includes a third plug-in connector member adapted to be connectable with said first plug-in connector member to circulate said disinfecting medium through a recirculation conduit branch, which is formed by a combination of at least said valve arrangement, said sampling and recirculating conduit including said first plug-in connector member, and said fluid inlet arrangement including said third plug-in connector member.

2. The hemodialysis device of claim 1, wherein said switching valve arrangement comprises a conduit branching member connected to said fluid outlet, an outlet valve connected between said branching member and said drain conduit, and a sample withdrawal valve connected between said branching member and said sampling and recirculating conduit, wherein said control unit is connected for control signal transmission to said outlet valve and to said sample withdrawal valve to alternatingly control said valves in time succession so that respectively one of said valves is open while the other of said valves is closed.

3. The hemodialysis device of claim 2, wherein said control unit controls said outlet valve and said sample withdrawal valve in a fixed time interval relationship relative to each other.

4. The hemodialysis device of claim 2, further comprising a volume measuring device connected for signal transmission to said control unit and interposed in said used fluid conduit to measure the volume of used fluid flowing through said used fluid conduit during an outlet valve open interval, wherein said control unit controls said sample withdrawal valve, during a sample withdrawal valve open interval directly following said outlet valve open interval, dependent upon said measured volume of used fluid.

5. The hemodialysis device of claim 4, wherein said control unit calculates a time duration of said sample withdrawal valve open interval based on said measured volume of used fluid.

6. The hemodialysis device of claim 4, wherein said volume measuring device comprises a balance chamber interposed in said used fluid conduit, wherein said control unit controls said outlet valve and said sample withdrawal valve based on a ratio of integer multiples of a volume of said balance chamber.

7. The hemodialysis device of claim 2, further comprising another valve having an inlet connected to said branching member and having an outlet, another conduit connected to said outlet of said another valve, and another plug-in connector member provided on a downstream end of said another conduit.

8. The hemodialysis device of claim 1, further comprising a sensor arranged to sense a connected state of said first plug-in connector member with said third plug-in connector member.

9. The hemodialysis device of claim 1, further comprising a container containing a disinfecting or cleaning solution concentrate and having an inlet connector member and an outlet connector member, wherein said first plug-in connector member and said inlet connector member are adapted to be connected together, and said third plug-in connector member and said outlet connector member are adapted to be connected together, so that said container containing a disinfecting or cleaning solution concentrate can be interposed between said sampling and recirculating conduit and said fluid inlet arrangement.

10. The hemodialysis device of claim 1, wherein said fluid inlet arrangement comprises a dialysis fluid preparation unit with a dialysis fluid outlet port connected to said upstream end of said fresh fluid conduit, a dialysis fluid concentrate inlet port, and a water inlet port, and comprises a water inlet container connected to said water inlet port, wherein said third plug-in connector member is arranged on said water inlet container.

11. The hemodialysis device of claim 1, wherein said first plug-in connector member comprises a lockable plug body and a fluid tapping needle protruding therefrom, said second plug-in connector member comprises a membrane that can be pierced by said fluid tapping needle, and said third plug-in connector member comprises a counter connector member adapted to be engaged by said lockable plug body.

12. The hemodialysis device of claim 1, further comprising a safety valve arranged at said third plug-in connector member.

13. The hemodialysis device of claim 1, wherein said fluid sample receiving container comprises a bag that is substantially non-permeable to gases.

14. A method for carrying out a controlled partial dialysate collection during a dialysis treatment and carrying out a recirculating disinfection cycle separately from said dialysis treatment in a hemodialysis device including a switching valve arrangement with an inlet port, a drain outlet port and a sampling outlet port, an element selected from the group consisting of a dialyzer and a shunt conduit connected upstream of said inlet port, and a dialysate fluid inlet arrangement connected upstream of said element selected from the group consisting of a dialyzer and a shunt conduit, said method comprising during said dialysis treatment: flowing used dialysate into said inlet port, alternatingly switching said valve arrangement so that said dialysate flowing into said inlet port alternatingly flows out of said drain outlet port during at least one drain period and out of said sampling outlet port during at least one sampling period, and collecting as a dialysate sample said dialysate flowing out of said sampling outlet port; and during said disinfection cycle connecting said outlet port to said fluid inlet arrangement, flowing disinfecting medium into said inlet port of said valve arrangement, and switching said valve arrangement so that said disinfecting medium flowing into said inlet port flows out of said sampling outlet port and to said fluid inlet arrangement.

15. The method of claim 14, wherein said hemodialysis device further includes a through-flow measuring device for said used dialysate arranged downstream of said element selected from the group consisting of a dialyzer and a shunt conduit, wherein said drain period has a prescribed fixed duration, and further comprising calculating the duration of said sampling period based on the quantity of said used dialysate measured by said through-flow measuring device during said drain period.

16. The method of claim 14, wherein said hemodialysis device further includes a through-flow measuring device for said used dialysate arranged downstream of said element selected from the group consisting of a dialyzer and a shunt conduit, wherein said switching of said valve arrangement is carried out so as to end said drain period and begin said sampling period when a predefined quantity of said used dialysate has been measured by said through-flow measuring device during said drain period.

17. The method of claim 16, wherein said measuring device comprises a balance chamber, and wherein said switching of said valve arrangement is carried out responsive to and when a predefined number of balance chamber strokes has been carried out.

18. The method of claim 14, wherein each said at least one sampling period has a predefined first fixed duration, each said at least one drain period has a predefined second fixed duration, and a respective one of said at least one sampling period and a respective one of said at least one drain period together make up a sample withdrawal time interval having a predefined third fixed duration equal to the sum of said first duration and said second duration.

19. The method of claim 18, further comprising calculating said predefined third fixed duration of said sample withdrawal time interval from a total duration of said dialysis treatment and a prescribed number of samples to be withdrawn during said dialysis treatment.

20. The method of claim 18, further comprising calculating said first fixed duration of said sampling period from the ratio of a prescribed total sample volume of said dialysate sample to be collected relative to a total dialysate volume flowing into said inlet port of said valve arrangement during said dialysis treatment, multiplied by said third fixed duration of said sample withdrawal time interval.

21. A method of operating a hemodialysis apparatus including a dialysate inlet arrangement, a valve arrangement having an inlet port, a drain outlet port and a sampling outlet port, at least one of a dialyzer and a shunt conduit connected between said dialysate inlet arrangement and said inlet port of said valve arrangement, a dialysate sample collecting container and a recirculation branch conduit selectively connecting said sampling outlet port for fluid flow to said dialysate inlet arrangement and to said dialysate sample collecting container, comprising the following steps:

during a dialysis treatment: flowing dialysate from said inlet arrangement through said dialyzer and into said inlet port, and then alternately flowing a first portion of said dialysate out of said sampling outlet port and into said dialysate sample collecting container during at least one sampling period and flowing a second portion of said dialysate out of said drain outlet port during at least one drain period; and during a recirculating disinfection cycle: flowing a disinfecting medium through said at least one of said dialyzer and said shunt conduit, into said inlet port, out of said sampling outlet port, through said recirculation branch conduit and to said dialysate inlet arrangement.

22. A hemodialysis apparatus for partial dialysate collection during a dialysis treatment and for recirculation disinfection during a disinfecting cycle, comprising a dialysate inlet arrangement, a used dialysate conduit, at least one of a dialyzer and a shunt conduit interposed between said inlet arrangement and said used dialysate conduit, a dialysate sample collection container, a recirculation fluid flow branch selectively connecting said used dialysate conduit to said dialysate inlet arrangement and to said dialysate sample collecting container, a drain conduit selectively connected to said used dialysate conduit, first means interposed between said used dialysate conduit and said recirculation fluid flow branch and said drain conduit for selectively directing a first portion of used dialysate from said used dialysate conduit to said recirculation fluid flow branch and a second portion of said used dialysate from said used dialysate conduit to said drain conduit during said dialysis treatment and for directing a disinfecting medium from said used dialysate conduit to said recirculation fluid flow branch during said disinfecting cycle, and second means interposed in said recirculation fluid flow branch for directing said first portion of said used dialysate into said dialysate sample collection container during said dialysis treatment and for directing said disinfecting medium into said dialysate inlet arrangement during said disinfecting cycle.

23. A hemodialysis device including a fresh fluid conduit with a fluid inlet arrangement at its upstream end, a used fluid conduit with a fluid outlet at its downstream end, and a fluid sampling and recirculating apparatus connected to said fluid outlet, wherein said apparatus comprises a drain conduit, a sampling and recirculating conduit with a first-plug-in connector member at a downstream end thereof, a switching valve arrangement connected to said fluid outlet and selectively connecting said fluid outlet for fluid flow to said drain conduit or to said sampling and recirculating conduit in exclusive alternating succession, a control unit connected for control signal transmission to said valve arrangement, and a fluid sample receiving container with a second plug-in connector member adapted to be connectable with said first plug-in connector member, and wherein said fluid inlet arrangement comprises a dialysis fluid preparation unit having a dialysis fluid outlet port connected to said upstream end of said fresh fluid conduit, a dialysis fluid concentrate inlet port, and a water inlet port, and a water inlet container that is connected to said water inlet port and that has a third plug-in connector member adapted to be connectable with said first plug-in connector member.

* * * * *

UNITED STATES PATENT AND TRADEMARK OFFICE
CERTIFICATE OF CORRECTION

PATENT NO. : 5,725,773
DATED : Mar. 10, 1998
INVENTOR(S) : Polaschegg

It is certified that error appears in the above-indentified patent and that said Letters Patent is hereby corrected as shown below:

On the title page, under [54], line 3, before "TOXINS" replace "OREMIC" by --UREMIC--;
under [56] References Cited, OTHER PUBLICATIONS, line 2, before "brochure" replace "Cart®," by --Cart™,--;

Col. 1, line 3, before "TOXINS" replace "OREMIC" by --UREMIC--;

Col. 3, line 9, after "Passiver" replace "Flüssigkeits-stromleiter" by --Flüssigkeitsstromteiler--.
line 29, after "partial" replace "streampump" by --stream pump--;

Col. 4, line 4, after "entitled" delete ""H";
line 5, before "("Hemodialysis" replace "ämodialysevorrichtung"" by --"Hämodialysevorrichtung"--;
line 10, after "von" delete "H";
line 11, before "mit" replace "ämodialysegeräten" by --Hämodialysegeräten--;

Col. 13, line 38, after "disinfection" replace "cycle" by --cycle:--;

Col. 15, line 9, after "a" (second occurrence) replace "first-" by --first--.

Signed and Sealed this

Eleventh Day of August 1998

Attest:

BRUCE LEHMAN

Attesting Officer    Commissioner of Patents and Trademarks